United States Patent [19]

Hendricks

[11] Patent Number: 5,067,941
[45] Date of Patent: Nov. 26, 1991

[54] ANTI-MOTION SICKNESS APPARATUS

[75] Inventor: Katherine A. Hendricks, Chicago, Ill.

[73] Assignees: Boris Tabakoff; John Newton, both of New Orleans, La. ; part interest to each

[21] Appl. No.: 527,139

[22] Filed: May 22, 1990

Related U.S. Application Data

[60] Division of Ser. No. 98,507, Sep. 17, 1981, Pat. No. 4,929,228, which is a continuation of Ser. No. 86, Jan. 2, 1987, abandoned, which is a continuation of Ser. No. 430,172, Sep. 30, 1982, abandoned.

[51] Int. Cl.$^5$ ............................................. A61M 21/00
[52] U.S. Cl. ....................................................... 600/27
[58] Field of Search ..................... 600/26, 27; 128/745, 128/897, 898; 33/451, 41; 40/406; 272/8 R, 8 N

[56] References Cited

U.S. PATENT DOCUMENTS 3,613,264 10/1971 Vitka et al. ......................... 434/126

Primary Examiner—Lee S. Cohen
Assistant Examiner—John P. Lacyk
Attorney, Agent, or Firm—Dressler, Goldsmith, Shore, Sutker & Milnamow, Ltd.

[57] ABSTRACT

The anti-motion sickness apparatus includes motion simulating means for providing a visually discernible wave motion image to create visually discernible orientation information for the user to confirm the inner ear information of the user, thereby preventing or at least greatly alleviating, the occurrence of motion sickness. A device helps position the motion simulating means in the field of view of the user. The method of use includes exposing the motion simulating means to the field of view of the user.

5 Claims, No Drawings

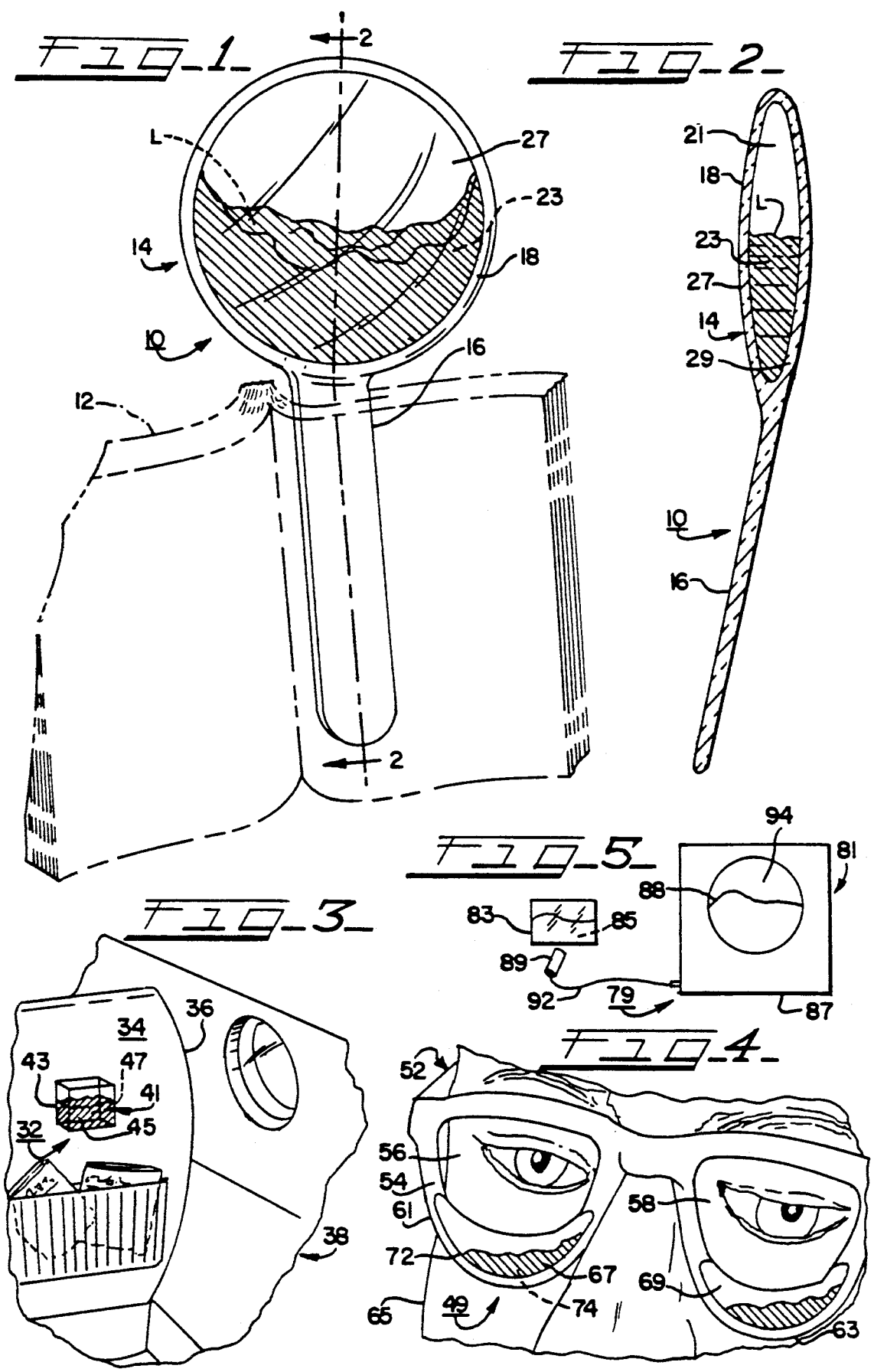

ANTI-MOTION SICKNESS APPARATUS

This is a division of application Ser. No. 098,507, filed on Sept. 17, 1987 now U.S. Pat. 4,939,228, which application is a continuation of Ser. No. 000,086, filed on Jan. 2, 1987, now abandoned which application, in turn, is a continuation of Ser. No. 430,172, filed on Sept. 30, 1982 now abandoned.

TECHNICAL FIELD

The present invention relates in general to an anti-motion sickness apparatus and a method of using it, and it more particularly relates to an apparatus and a method of using it for preventing, or at least retarding greatly, the occurrence of motion sickness.

BACKGROUND ART

There have been a number of different pharmaceutical products that have been used and have been variously effective for preventing, or at least tending to prevent, motion sickness, which typically occurs while a person travels in a vehicle such as an airplane, automobile, boat or the like. For example, reference may be made to U.S. Pat. No. 4,070,463, and the book entitled, "Motion Sickness" by J. T. Reason and J. J. Brand, published by Academic Press, 1975.

While drugs have proven to be an effective remedy, they have all suffered from various disadvantages. For example, at least some of the drugs have produced undesirable side effects, such as drowsiness. Such diminishing of mental alertness is not at all tolerable for some applications, such as the use by military personnel of the armed forces, as well as air craft pilots and other vehicle operators. In the case of the armed forces, military personnel must remain acutely aware at all times to function properly, and thus pharmaceutical products have not at all been entirely satisfactory as a remedy to motion sickness.

Another disadvantage of the use of drugs in attempting to prevent motion sickness, is the fact that the drugs must be taken a predetermined time prior to traveling. For example, pharmaceutical products typically must be taken one hour prior to traveling. Sometimes persons forget, or are otherwise unable to ingest the drugs at the prescribed time prior to traveling. Thus, the drugs are not always effective at the time of susceptibility to motion sickness.

Yet another disadvantage of the use of drugs in attempting to alleviate motion sickness, is the difficulty encountered when such drugs are administered to children. In this regard, it is usually required to adjust the size of the dosage to the body size of the child. It is oftentimes difficult to make such an adjustment in an accurate manner, and thus there may be the risk of not providing effective dosages, or of an overdosage resulting in unwanted and undesirable side effects.

Therefore, it would be highly desirable to have an apparatus, and a method of using it, to prevent, or to at least greatly retard the effect of motion sickness, without the need of taking drugs. Such a technique should have little or no side effects, and should be highly effective. The user should remain mentally aware without becoming drowsy.

The technique should be convenient to use, and the apparatus should be relatively inexpensive to manufacture. Unlike the use of drugs, the apparatus should be able to be used repeatedly so that there would be no need to replenish the supply of the product by the user. In this regard, the user would need to make only a single purchase of the apparatus, which could be used repeatedly without being consumed.

The technique should be effective immediately without the need to take precautions prior to traveling as is the case when taking drugs. Also, the technique should be equally effective without side effects for both children and adults, regardless of body size or weight.

DISCLOSURE OF THE INVENTION

Therefore, the principal object of the present invention is to provide a new and improved anti-motion sickness apparatus and a method of using it, in a highly effective manner to prevent or at least greatly alleviate the occurrence of motion sickness with little or no side effects and without the taking of pharmaceutical products.

Another object of the present invention is to provide such a new and improved anti-motion sickness apparatus and a method of using it, for both adults and children alike, without the need for compensating for body weight or size, and without the need for taking precautions prior to traveling.

A further object of the present invention is to provide such a new and improved anti-motion sickness apparatus and a method of using it, which apparatus can be used repeatedly without consuming it, and which apparatus is relatively inexpensive to manufacture and convenient to use.

Briefly, the above and further objects of the present invention are realized by providing a novel apparatus, which is used by exposing it to the view of the user to become immediately effective to prevent, or alleviate the occurrence of motion sickness.

The anti-motion sickness apparatus includes motion simulating means for providing a visually discernible wave motion image to create visually discernible orientation information for the user to confirm the inner ear information of the user, thereby preventing or at least greatly alleviating, the occurrence of motion sickness. A device helps position the motion simulating means in the field of view of the user. The method of use includes exposing the motion simulating means to the field of view of the user.

The motion simulating means causes no known side effects. In this regard, it does not make the user drowsy, since it does not hypnotize the user, and since it does not require the use of drugs.

It is effective immediately upon use. It does not require precautions prior to traveling.

The apparatus and method of use is equally safe and effective for both adults and children alike, regardless of the size or weight of the user. The apparatus is relatively inexpensive to manufacture, and it is very convenient to use.

BRIEF DESCRIPTION OF THE DRAWINGS

The above-mentioned and other objects and other features of this invention and the manner of attaining them will become apparent, and the invention itself will be best understood by reference to the following description of embodiments of the invention taken in conjunction with the accompanying drawings, wherein:

FIG. 1 is a pictorial view of an anti-motion sickness apparatus, which is constructed in accordance with the present invention, and which is illustrated being used as a bookmark during reading;

FIG. 2 is a sectional elevational view of the apparatus of FIG. 1 taken substantially on line 2—2 thereof;

FIG. 3 is a pictorial view of another anti-motion sickness apparatus, which is constructed in accordance with the present invention, and which is illustrated being used in an aircraft;

FIG. 4 is a pictorial view of still another anti-motion sickness apparatus, which is constructed in accordance with the present invention, and which is illustrated in the form of spectacles; and FIG. 5 is a pictorial, partly schematic, view of a further anti-motion sickness apparatus, which is constructed in accordance with the present invention, and which is in the form of an electrical display system.

BEST MODE FOR CARRYING OUT THE INVENTION

Referring now to the drawings, and more particularly to FIGS. 1 and 2 thereof, there is shown an anti-motion sickness apparatus 10, which is constructed in accordance with the present invention, and which is adapted to be used while reading a book, such as a book 12. Oftentimes, motion sickness occurs when a person is reading while riding in a vehicle (not shown).

The apparatus 10 generally comprises a motion simulating device 14, which provides a visually discernible wave motion image to create visually discernible orientation information for the user to confirm the inner ear information, so that the occurrence of motion sickness is prevented, or at least greatly alleviated. An elongated, flat stem or strip 16 is integrally connected at its upper end to the motion simulating device 14 and is adapted to be inserted between the pages of the book 12 to help position the motion simulating device 14 in the field of view of the user.

The motion simulating device 14 includes a flat circular container 18 composed of translucent material, such as suitable plastic material. As shown in FIG. 2, the container 18 has a hollow interior 21 for confining a visually discernible fluid in the form of a colored liquid 23 and for permitting it to move therein during motion of the container 18. As a result, the user can view the liquid 23 through the translucent contained 18, and observe the motion of the liquid 23 within the hollow interior 21. In this regard, the hollow interior 21 is only partially filled to permit the liquid 23 to flow freely and move thereabout during the motion of a vehicle in which the user is riding.

The occurrence of motion sickness is prevented, or at least alleviated, since motion sickness is caused in a person by the fluid in the inner ear sensing motion by means of inertia, while the eyes fail to sense such motion visually. Thus, the brain experiences a mismatch or conflict between the inertial and the visual frames of reference, and the symptoms of motion sickness are triggered thereby. The symptoms include nausea, pallor, sweating and others.

When a person is exposed to conditions of conflicting inertial and visual frames of reference, the discrepancy is detected by the person and the mismatch condition affects the neurophysiological and biochemical mechanisms which in turn cause motion sickness to occur in the person. Thus, by employing the apparatus 10, of the present invention, the maladaptation of the person is corrected, or prevented, since the person visually perceives apparent motion when viewing the motion simulating device 14, thereby preventing the mismatch from occurring. In this regard, the motion simulating device 14 visually communicates the orientation information to the brain via the eyes of the user on a real time basis, in that there is no delay or lag time from the time of generation of the wave motion image, to the visual perception of such image. The visually perceived orientation information then confirms the inner ear generated information regarding spatial orientation. Thus, the combination of the visual and inner ear information, the one confirming the other, prevents the occurrence of motion sickness.

Considering now the apparatus 10 in greater detail, the motion simulating device 14 is generally circular in configuration and includes front and rear circular walls 27 and 29. Each one of the walls is dished and is connected together at their peripheral edges by any suitable technique, such as heat welding or applying a suitable adhesive.

The circular configuration of the walls 27 and 29 enable tho level L of the fluid 23 to appear as a horizontal line relative to the circular appearance of the walls 27 and 29. Thus, as best seen in FIG. 1, the motion of the liquid 23 in the interior 21 causes a wave motion of the liquid to be established at the level L to simulate visually the movement of the user, as the user rides in a vehicle.

The liquid 23 is preferably water having a suitable dye added to it. The dye may be a relaxing and peaceful color, such as green. As will become apparent to those skilled in the art, other liquids may also be used, such as mercury. Suitable anti-freeze solvents may also be added.

The stem 16 is in the form of a flat, rigid elongated member integrally fixed to, and extending from the walls 27 and 29, where they are joined together at the bottom portion thereof. The stem 16 is inclined forwardly from the plane of the container 18. In this manner, when the stem 16 is positioned between the pages of the opened book 12, as shown in FIG. 1, the motion simulating device 14 is positioned above the pages of the book 12 at an angle inclined angularly forwardly relative to the stem 16 and the pages of the book to help position the device 14 in the field of view of the user. In this regard, as the user reads the book 12, the device 14 is disposed within at least the peripheral vision of the user to achieve the desired effect.

The apparatus 10 is used by inserting the stem 16 thereof between the pages of the book 12 in the field of view of the user. Nothing further need be done. Alternatively, the stem 16 may be held in the hand in a position within the field of view of the user.

Referring now to FIG. 3, there is shown an anti-motion sickness apparatus 32, which is constructed according to the present invention, and which is generally similar to the apparatus 10, except that the apparatus 32 is adapted to be mounted on the back 34 of a seat 36 of an aircraft 38. The apparatus 32 functions in a similar manner as the apparatus 10, and includes a motion simulating device 41, which provides a visually discernible wave motion image to create visually discernible orientation information to a person (not shown) seated behind the seat 36. In this manner, the visual orientation information confirms the inner ear information to prevent, or at least retard greatly, the occurrence of motion sickness in the person. Mounting means (not shown) in the form of a suitable adhesive is used to fix the device 41 to the back 34 of the seat to help position the device 41 in the field of view of the user.

The device 41 includes a container 43, which is composed of translucent material, such as suitable plastic material. The container 43 is box-shaped and has a generally rectangular front wall 45. The container has a hollow interior, which is partly filled with a fluid in the form of a liquid 47. The liquid 47 is mercury, and is exposed to view through the translucent walls of the container 43. It should be understood that only a portion of the container need be translucent and not necessarily transparent, so that the motion of the liquid is visually discernible to the user.

Referring now to FIG. 4, there is shown an anti-motion sickness apparatus 49, which is constructed according to the present invention, and which is in the form of spectacles 52 to serve the same function as the apparatus 10. The spectacles 52 include a plastic frame 54, having occular lenses 56 and 58 surrounded by respective frame portions 61 and 63. The spectacles 52 are supported on the head of a user 65 in a conventional manner.

The spectacles 52 includes a pair of wave motion simulating devices generally indicated at 67 and 69 mounted in the lower portion of the frame portions 61 and 63, which serve to help position the devices 67 and 69 in the field of view of the user. The devices, such as the device 67, each includes a container 72 mounted in the bottom portion of the frame portion 61 and is in the form of a hollow space or interior confining a fluid in the form of a colored liquid 74, to serve the same purpose as the liquid 23 in the container 18 of the apparatus 10. The material of the frame 54 is transparent, and thus the liquid 74 is exposed to the peripheral field of view of the user 65.

Referring now the FIG. 5, there is shown an anti-motion sickness apparatus 79, which is constructed according to the present invention, and which is an electrical version of the apparatus of FIG. 1. The apparatus 79 includes a motion simulating device 81, which provides a visually discernible wave motion image to create visually discernible orientation information for the user to confirm the inner ear information of the user, thereby preventing or at least greatly retarding, the occurrence of motion sickness.

The device 81 includes a transparent container 83, being partially filled with a colored liquid 85, similar to the device 41 of FIG. 3, for producing a wave motion image, and a display unit 87 for displaying a display image 88, which is a reproduction of the wave motion image produced by the liquid 85 in the container 83, to a larger scale at a remote location. A sensing device 89 converts the moving image of the wave motion of the liquid 85 to electrical signals and supplies them via a cable 92 to the remotely located unit 87 to enable it to produce the display image 88. Thus, the device 89 and the cable 92 serve to help position the unit 87 of the wave motion simulating device 81 in the field of view of the user.

The unit 87 is a television receiver having a cathode ray tube 94 for producing the image 88. The sensing device 89 is a television camera. It will become apparent to those skilled in the art that, in place of the cable 92, the camera 89 can transmit the signals to the receiver 87, and there may be a plurality of such receivers (not shown). Also, the reproduced image may be projected onto a screen (not shown), if it is desired to enlarge the size of the moving image.

While particular embodiments of the present invention have been disclosed, it is to be understood that various different modifications are possible and are contemplated within the true spirit and scope of the appended claims. For example, instead of the television apparatus of FIG. 5, a suitable projection system may be employed to directly enlarge the desired image, as will become apparent to those skilled in the art. There is no intention, therefore, of limitations to the exact abstract or disclosure herein presented.

I claim:

1. An anti-motion sickness apparatus for use in a moving vehicle and comprising
   a vehicular motion sensing means adapted to be mounted to said vehicle and providing an electrical signal output indicative of the sensed vehicular motion; and
   a vehicular motion simulating display means responsive to said electrical signal output and positioned within the field of vision of a user of said vehicle;
   said vehicular motion simulating display means providing a wave motion image visible to the user and corresponding substantially to the vehicular motion sensed by said sensing means.

2. The anti-motion sickness apparatus in accordance with claim 1 wherein said sensing means is situated in the vehicle at a location remote from said display means.

3. The anti-motion sickness apparatus in accordance with claim 1 wherein the vehicular motion simulating display means is a cathode ray tube.

4. The anti-motion sickness apparatus in accordance with claim 1 wherein the vehicular motion sensing means includes a television camera.

5. The anti-motion sickness apparatus in accordance with claim 1 wherein said vehicular motion sensing means comprises a closed container having a translucent portion and confining therewithin a visually discernible liquid that can move freely within the container as a result of an inertial force related to the motion of the vehicle and generate visually discernible orientation information directly indicative of the motion of the vehicle, and a television camera converting the generated visually discernible orientation information to an electrical signal output, and wherein said vehicular motion simulating display means is a television receiver operably associated with said television camera to receiver said electrical signal output and positioned within said field of vision of the vehicle user.

* * * * *